United States Patent
Rolfes Meyering

(10) Patent No.: US 8,932,694 B2
(45) Date of Patent: Jan. 13, 2015

(54) FLUORINATED POLYMERS AND LUBRICIOUS COATINGS

(75) Inventor: Emily R. Rolfes Meyering, Eden Prairie, MN (US)

(73) Assignee: Surmodics, Inc., Eden Prairie, MN (US)

( * ) Notice: Subject to any disclaimer, the term of this patent is extended or adjusted under 35 U.S.C. 154(b) by 443 days.

(21) Appl. No.: 13/171,687

(22) Filed: Jun. 29, 2011

(65) Prior Publication Data
US 2011/0318575 A1    Dec. 29, 2011

Related U.S. Application Data

(60) Provisional application No. 61/359,691, filed on Jun. 29, 2010.

(51) Int. Cl.
| | |
|---|---|
| A61M 25/00 | (2006.01) |
| C08F 14/18 | (2006.01) |
| C08F 26/10 | (2006.01) |
| C08F 226/10 | (2006.01) |
| A61L 29/08 | (2006.01) |
| C08F 6/00 | (2006.01) |
| A61L 27/16 | (2006.01) |
| A61L 29/04 | (2006.01) |
| A61L 31/10 | (2006.01) |
| C08F 220/24 | (2006.01) |
| C08F 220/36 | (2006.01) |
| C08F 220/60 | (2006.01) |

(52) U.S. Cl.
CPC ...... *C08F 226/10* (2013.01); *A61M 2025/0047* (2013.01); *A61L 27/16* (2013.01); *A61L 29/085* (2013.01); *A61L 31/10* (2013.01); *A61L 2400/10* (2013.01); *C08F 6/003* (2013.01); *C08F 220/24* (2013.01); *C08F 220/36* (2013.01); *C08F 220/60* (2013.01)
USPC .......................... 428/36.91; 428/336; 428/421

(58) Field of Classification Search
None
See application file for complete search history.

(56) References Cited

U.S. PATENT DOCUMENTS

| | | | |
|---|---|---|---|
| 5,002,582 A | 3/1991 | Guire et al. | |
| 5,414,075 A | 5/1995 | Swan et al. | |
| 5,563,056 A | 10/1996 | Swan et al. | |
| 5,637,460 A | 6/1997 | Swan et al. | |
| 5,714,360 A | 2/1998 | Swan et al. | |
| 5,858,653 A | 1/1999 | Duran et al. | |
| 6,156,345 A | 12/2000 | Chudzik et al. | |
| 6,278,018 B1 | 8/2001 | Swan | |
| 6,497,729 B1 | 12/2002 | Moussy et al. | |
| 6,530,950 B1 * | 3/2003 | Alvarado et al. | 623/1.13 |
| 6,706,408 B2 | 3/2004 | Jelle | |
| 7,345,123 B2 | 3/2008 | Qiu et al. | |
| 7,348,055 B2 | 3/2008 | Chappa et al. | |
| 7,357,793 B2 | 4/2008 | Pacetti | |
| 2003/0055479 A1 * | 3/2003 | Jayaraman | 623/1.1 |
| 2005/0234205 A1 | 10/2005 | Yamaguchi et al. | |
| 2010/0016533 A1 | 1/2010 | Pacetti | |

FOREIGN PATENT DOCUMENTS

| | | |
|---|---|---|
| EP | 0 398 250 | 11/1990 |
| WO | WO 2005/049678 | 6/2005 |
| WO | WO 2006/026521 | 3/2006 |
| WO | WO 2009/009280 | 1/2009 |

OTHER PUBLICATIONS

PCT Search Report for International Application No. PCT/US2011/042282 mailed on Jan. 2, 2012.

Církva, V., et al., (2003) *Fluorinated epoxides 6. Chemoselectivity in the preparation of 2-[(heptafluoroisopropyl)methyl] oxirane from iodoacetate and iodohydrin precursors*, Journal of Fluorine Chemistry 121:101-104.

Lopérgolo L., et al. (2003) *Direct UV photocrossinglinking of poly(N-vinyl-2-pyrrolidone) (PVP) to produce hydrogels*, Polymer 44: 6217-6222.

* cited by examiner

Primary Examiner — Ramsey Zacharia
(74) Attorney, Agent, or Firm — Kagan Binder, PLLC

(57) ABSTRACT

The invention provides fluorinated polymeric articles formed a composition including a fluoropolymer. The fluoropolymer is formed using a fluorinated monomer that provides the fluoropolymer with most or all of the fluorine atoms not directly covalently attached to an atom of the fluoropolymer backbone. The fluoropolymer can also include a non-fluorinated hydrophilic monomer in a weight amount greater than the fluorinated monomer. The fluoropolymer composition also includes an ultraviolet light (UV)-reactive group capable of covalent bonding to promotes formation of the fluorinated polymeric article. The fluorinated polymeric article can be in the form of a durable lubricious coating on the surface of an implantable medical device. Coatings of the invention exhibit excellent wet/dry lubricity, durability, and controlled swelling.

22 Claims, No Drawings

FLUORINATED POLYMERS AND LUBRICIOUS COATINGS

PRIORITY CLAIM

This application claims the benefit of U.S. Provisional Patent Application Ser. No. 61/359,691, filed Jun. 29, 2010, entitled FLUORINATED POLYMERS AND LUBRICIOUS COATINGS, the disclosure of which is incorporated herein by reference.

FIELD

The invention relates to fluoropolymers including hydrophilic monomers. The invention also relates to lubricious polymeric coatings for surfaces of medical articles.

BACKGROUND

Implantable and insertable medical devices are commonly used in the body at various locations. Implantable medical devices are described as those that are delivered to a target site in the body and designed to reside at that site for a period of time to affect treatment of an individual. Examples of these implantable devices include prosthetic devices such as stents. Insertable medical devices refer to those in which a portion or the entire device is introduced into the body, but that are not necessarily required to reside at the target location in the body for an extended period of time. Insertable medical devices can include those that are moved in the body, such as to deliver a fluid, drug, or an implantable medical device to a target location in the body. Examples of insertable devices include catheters, endoscopes, cystoscopes, guidewires, needles, trocars, and the like.

Many implantable or insertable medical devices are used in processes where they are moved against body tissue. For example, these devices are often moved against the lining of a body lumen, such as one in the cardiovascular system (e.g., an artery or vein), or one in the urogenital system, such as the urethra, or fallopian tube. As a general matter, it is desirable to provide a device surface that minimizes trauma to tissue that it is moved against.

However, implantable or insertable medical devices are typically fabricated from biocompatible metals or certain plastic materials that inherently do not possess a low friction or lubricious surface. To address this, lubricants and coatings have been used to reduce the frictional forces that facilitate movement of the device in relation to body tissue.

One approach to providing a lubricious surface on implantable or insertable medical devices has been to immobilize a hydrophilic polymer such as poly(ethylene glycol), poly (acrylamide,) or poly(vinylpyrrolidone) on the surface of the device. These polymers attract water, and become slick upon hydration, resulting in a device surface that has "wet" lubricity. However, these types of coatings can swell substantially and increase the coating thickness when hydrated. Also, since lubricity relies on these being substantially hydrated, lubricity can be lost if water is squeezed out of the coating.

Rather than using a hydrophilic "wet" low friction coating, the medical device may be fabricated from using a material such as polytetrafluoroethylene (PTFE) which can provide a low friction "dry" surface. PTFE is well-known for its chemical resistance, high temperature stability, resistance against ultra-violet radiation, low friction coefficient and low dielectric constant, among other properties. As a result, it has found numerous applications in harsh physico-chemical environments and other demanding conditions. For example, in some cases, one approach has been to provide a polytetrafluoroethylene (PTFE) coating, which provides a "dry lubricity" to the device surface. Although the PTFE displays excellent low frictional properties, it can be very difficult to make coatings or portions of devices from PTFE because of its high melting point. In addition, PTFE repels water, and although low friction, the lubricity is not enhanced when contacted with water which is present in body fluid in contact with a device surface.

Applicants have found that it would be highly desirable to provide coatings that have both properties of dry and wet lubricity, and that also display one or more properties such as biocompatibility, durability, and compliance. The novel fluoropolymer and fluoropolymer-containing compositions disclosed herein provide these features and represent distinct improvements in the art of low friction coatings for medical devices.

SUMMARY

The present invention is related to novel fluoropolymers, and also to polymeric articles made using these fluoropolymers. The novel fluoropolymers are particularly useful in association with medical devices, such as coatings on implantable or insertable medical devices.

The fluoropolymer-based polymeric compositions disclosed herein offer distinct advantages for use in the body. For example, the compositions can be used to prepare coatings that have excellent physical properties and that enhance the use of a coated medical device in the body. Advantages provided by the coatings include one or more of the following: excellent durability, resistance to delamination, compliance, controlled swelling, and excellent wet/dry lubricity.

The fluoropolymers and fluoropolymer-containing compositions can provide polymeric matrices displaying properties of both wet and dry lubricity. Reactive chemistries included in the fluoropolymers or fluoropolymer-containing composition can also improve matrix properties, such as durability and/or adhesion, which can be useful when the matrix is in the form of a coating on the device surface. To provide these properties, the composition uses one or more polymers comprising a fluorinated monomer, a non-fluorinated hydrophilic monomer, and a monomer or compound that is activatable upon exposure to an external stimulus to provide covalent bonding of the polymeric material in the composition and/or to a device. In some cases the composition uses a hydrophilic monomer that is both hydrophilic and that is capable of being activated upon exposure to an external stimulus to provide covalent bonding.

Applicants have discovered that using a fluorinated monomer which provides a fluoropolymer wherein most or all of the fluorine atoms of the fluoropolymer are spaced away from the polymeric backbone can form a polymeric matrix with improved lubricity and durability. That is, most or all of the fluorine atoms of the fluoropolymer are directly covalently attached to atoms of the polymer that are not part of the primary linear chain of atoms defining the polymer backbone. It is thought that this particular arrangement of fluorine atoms in the fluoropolymer significantly enhances the presentation of fluorine atoms in combination with the non-fluorinated hydrophilic monomer and the activatable monomer or compound in the composition. The particular use of these types of fluoromonomers in combination with hydrophilic and reactive components more effectively utilizes fluorine chemistries present in the composition for providing a lubricious surface.

When the composition is used to form a coating, a significant improvement in lubricity is observed, along with the ability of the coated material to remain durably attached to a device surface. In addition, the coating can exhibit controlled swellability, which is advantageous for the movement of a device in the body.

While the fluoropolymers currently disclosed are useful for the preparation of coatings, other embodiments contemplate use of the fluoropolymers for the preparation of other article forms, such as structural portions of articles that are inserted or implanted into the body.

The coatings or articles can be formed from a single fluoropolymer or a blend of two or more polymers including the fluoropolymer. If a blend of polymers is used, then monomeric components featured in the polymeric composition can be on the same or on different polymers.

In some embodiments, the composition includes a polymer having a monomer that includes one or more chemical groups that are activatable upon exposure to an external stimulus, such as UV light. For example, the fluoropolymer can include pendent latent-reactive UV photogroups that can be activated to undergo covalent bonding to a target substrate. In other embodiments, the composition includes a non-polymeric component that includes chemical groups that are activatable upon exposure to an external stimulus, such as UV light.

One embodiment provides a durable lubricious coating comprising one or more polymers comprising at least one fluoropolymer. The fluoropolymer has a polymeric backbone and includes a fluorinated monomer comprising fluorine atoms, wherein the majority or all of the fluorine atoms in the fluorinated polymer are not directly covalently attached to an atom of the fluoropolymer's backbone. The coating also includes a non-fluorinated hydrophilic monomer which can be present in the fluoropolymer, or in a second polymer, or in both in the fluoropolymer and the second polymer. The composition also includes an ultraviolet light (UV)-reacted group that covalently bonds polymeric material in the coating. The UV-reacted group can be present as part of the fluoropolymer, as part of the second polymer, or present in a non-polymeric compound.

The fluoropolymer-containing coatings disclosed herein demonstrate excellent wet/dry lubricity and remain durable, even after having been placed under physical challenge. A coating having these properties is particularly useful for implantable medical devices, such as catheters, that experience considerable frictional forces during use. In these cases, the fluoropolymer-containing coating can be less likely to be abraded when the coated device is manipulated after insertion into body. That is, the coating can be unlikely to fragment and produce coating residue that could be lost in vivo upon movement of device. Therefore, this feature (residue minimization) in turn provides related advantages, such as increased patient safety, extended use of the device life, and improved function of the device.

Some embodiments of the fluoropolymer-containing coatings are also advantageous for use in areas of the body where traditional hydrophilic coatings fail to retain enough water to provide sufficient lubricity. As such, the fluoropolymer-containing coatings can provide improvements with regards to implantation or insertion procedures wherein the medical article can be moved against tissue.

Another embodiment, provides a composition that includes one or more polymers with one of the one or more polymers being a fluoropolymer. The fluoropolymer has a polymeric backbone and includes a fluorinated monomer comprising fluorine atoms, wherein the majority or all of the fluorine atoms in the fluorinated polymer are not directly covalently attached to an atom of the fluoropolymer's backbone. The composition also comprises a non-fluorinated hydrophilic monomer which can be present in the fluoropolymer, or in a second polymer, or in both the fluoropolymer and second polymer. The composition also includes an ultraviolet light (UV)-activatable group capable of covalently bonding to a target moiety upon exposure to UV radiation, the UV-activatable group present in the fluoropolymer, in a second polymer, or in a non-polymeric compound.

Another aspect of the embodiments disclosed herein provide a fluoropolymer. The fluoropolymer has a polymeric backbone and comprises a fluorinated monomer comprising fluorine atoms. The majority of, or all of the fluorine atoms in the fluorinated monomer are not directly covalently attached to an atom of the polymer backbone. The fluoropolymer also includes a non-fluorinated hydrophilic monomer. The fluoropolymer also includes a monomer comprising an ultraviolet light (UV)-activatable group capable of covalently bonding to a target moiety upon exposure to UV radiation.

In some aspects, the fluoropolymer comprises a fluorinated monomeric unit of formula I:

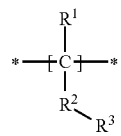

wherein $R^1$ is —H, —F, —CH$_3$, or —CH$_2$CH$_3$, $R^2$ is —(a covalent bond), or a non-fluorinated linking group comprising one or more of C, O, N, or S, and $R^3$ is a fluorocarbon group, wherein the amount of fluorine atoms provided in $R^3$ in the polymer is greater than an amount of any fluorine atoms attached to atoms directly of the polymer backbone.

In some aspects, the fluoropolymer or fluoropolymer-containing composition can include a non-fluorinated hydrophilic monomer in an amount by weight greater than the fluorinated monomer of formula I.

Other embodiments of the present disclosure provide an insertable or implantable medical article comprising the fluoropolymer, or an insertable or implantable medical article formed by a process using compositions disclosed herein. In yet other aspects, a method of treating a subject is provided comprising using an insertable or implantable medical article formed including the fluoropolymer or composition of the invention, or having a fluoropolymer-containing coating of the invention, in a subject.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The present disclosure is directed to fluoropolymers, compositions including fluoropolymers, and articles formed using the fluoropolymers, such as durable lubricious coatings for implantable or insertable medical devices. Generally, the fluoropolymer of the invention use a fluorinated monomer comprising fluorine atoms, wherein the majority or all of the fluorine atoms in the fluorinated monomer are not directly covalently attached to an atom of the polymer backbone. The fluoropolymer also includes a non-fluorinated hydrophilic monomer. The non-fluorinated hydrophilic monomer can be present in the fluoropolymer in an amount by weight that can be greater than the fluorinated monomer.

In some aspects, the fluoropolymer includes a monomer comprising an ultraviolet light (UV)-activatable group capable of covalently bonding to a target moiety upon exposure to UV radiation. If the fluoropolymer does not include this ultraviolet light (UV)-activatable group, it can be included in a composition that includes the photopolymer, such as on a non-polymeric component, or a second polymeric component.

Compositions disclosed herein can include polymeric material that can be in the form of a single fluoropolymer, or can include a blend of polymeric material wherein at least one polymer in the blend can be a fluoropolymer.

As a general matter, a composition of the invention includes the components of (1) a fluoropolymer that includes a fluorinated monomer including one or more fluorine atoms, wherein the majority or all of the fluorine atoms in the fluorinated monomer are not directly covalently attached to an atom of the polymer backbone; (2) at least one non-fluorinated hydrophilic monomer present in the fluoropolymer, and (3) an ultraviolet light (UV)-activatable group capable of covalently bonding to a target moiety upon exposure to UV radiation. The UV-activatable group can be present on a monomer in the fluoropolymer, on a monomer in an optional second polymer, or on an optional non-polymeric compound. In some aspects, the non-fluorinated hydrophilic monomer can be present in an amount by weight greater than the fluorinated monomer.

The composition can include a fluoropolymer wherein all three components, the fluorinated monomer, the non-fluorinated hydrophilic monomer, and the ultraviolet light (UV)-activatable group are present in the fluoropolymer. In some cases, the composition includes a fluoropolymer that includes at least three different monomer types: a fluorinated monomer, a non-fluorinated hydrophilic monomer, and a monomer comprising a pendent ultraviolet light (UV)-activatable group. Other monomer types can be present in the fluoropolymer, such as ones that provide pendent charged groups, such as pendent anionic groups (e.g., sulfonate groups). A fluoropolymer including these three monomeric components can be used as the predominant polymeric material in the composition, or can be used in a blend with one or more other polymers.

In some cases, the composition includes a fluoropolymer that includes two different monomer types: a fluorinated monomer and a non-fluorinated hydrophilic monomer. In this fluoropolymer preparation, the non-fluorinated hydrophilic monomer provides a dual function in that it can be hydrophilic and also capable of being activated and bonding to a target moiety upon exposure to ultraviolet light (UV). One non-fluorinated hydrophilic monomer capable of being UV activated and bonded to a target moiety is vinyl pyrrolidone.

As a general matter, the fluoropolymer has a sufficient amount and type of polymer forming material (monomers) to provide a desired hydrophile balance. The fluoropolymer can be dissolvable in a polar liquid, such as water or an alcohol, like isopropanol. In some aspects, the fluoropolymer can also have a sufficient amount of hydrophilic monomers to make it blendable with another hydrophilic polymer.

As used herein, a polymer having "hydrophilic" properties can be soluble in water. Accordingly, a coating prepared from a hydrophilic polymer can be wetted and retain water. The hydrophilicity of a polymer can be described in terms of how soluble the polymer is in water. A coating can be described in terms of the amount of water the coating can retain when wetted.

In some aspects, the fluoropolymer has a solubility in water of about 0.5 mg/mL or greater, about 1 mg/mL or greater, about 5 mg/mL or greater, or about 10 mg/mL or greater. Highly water-soluble fluoropolymers of the invention may have a solubility up to about 500 mg/mL or greater.

In some aspects, the fluoropolymer can include one or more monomer(s) that increase the fluoropolymer's solubility in polar protic solvents, such as alcohols like butanol, isopropanol, n-propanol, ethanol, and methanol, or polar aprotic solvents like acetone and ethyl acetate. Exemplary monomers include those having hydrophobic moieties such as dimethylacrylamides, diisopropylacrylamides, tert-butylacrylamides, and medium chain (e.g., C—C) alkyl acrylamides. A composition including the fluoropolymer and a polar protic or aprotic solvent can be useful for coating substrates formed from silicone or other polymers on which water does not sheet out well on.

In the least, fluoropolymers of the invention have a polymeric backbone and include a fluorinated monomer and a non-fluorinated hydrophilic monomer. In the fluorinated monomer, the majority of, or all of the fluorine atoms, are not directly covalently attached to an atom of the polymer backbone (the backbone being represented by a linear chain of atoms in the polymer). In some aspects, the percentage by weight of the non-fluorinated hydrophilic monomer can be greater than the fluorinated monomer in the fluoropolymer.

As used herein, "non-backbone" fluorine atoms are spaced away from an atom of the polymeric backbone by at least one atom. The following monomeric unit formula exemplifies "non-backbone" fluorine atoms:

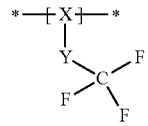

wherein X is an atom of the polymeric backbone, Y is single atom or a group of atoms connecting the trifluorocarbon group ($CF_3$) to the polymeric backbone. The fluorine atoms of the trifluorocarbon group are examples of "non-backbone" fluorine atoms. Trifluoroethyl methacrylate is a specific example of a monomer that can provide a fluoropolymer with three non-backbone fluorine atoms, and no backbone fluorine atoms, per respective monomeric unit.

On the other hand a "backbone" fluorine atom is directly covalently attached to an atom of the polymeric backbone. Tetrafluoroethylene produces a monomer, as shown below, having two "backbone" fluorine atoms.

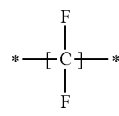

Optionally, fluoropolymers of the invention can include one or more "backbone" fluorine atom(s). However, if "backbone" fluorine atoms are present in the fluoropolymer, they are present in a molar amount less than the "non-backbone"

fluorine atoms. As a specific example, a fluoropolymer of the invention can include non-backbone fluorine-providing monomers such as trifluoroethyl methacrylate, wherein the trifluoroethyl methacrylate can be the fluorine-providing monomer in the fluoropolymer. Another specific example can be a fluoropolymer prepared using a non-fluorinated hydrophilic monomer, and an equimolar amount of trifluoroethyl methacrylate and tetrafluoroethylene. In this fluoropolymer, the ratio of non-backbone to backbone fluorine atoms is 3:2.

The fluoropolymer of the invention can be formed by any suitable mode of synthesis, including addition or condensation polymerizations. In one mode of practice the fluoropolymer can be formed by the free radical polymerization of fluorinated monomers and non-fluorinated hydrophilic monomers.

In one mode of practice the fluoropolymer can be prepared using a fluoromonomer according to formula II, which provides non-backbone fluorine atoms to the fluoropolymer:

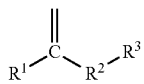

II wherein $R^1$ is —H, —F, —CH$_3$, or —CH$_2$CH$_3$, $R^2$ is —(a covalent bond), or a non-fluorinated linking group comprising one or more of C, O, N, or S, and $R^3$ is a fluorocarbon group.

In some aspects, $R^1$ is —H, —CH$_3$, or —CH$_2$CH$_3$, and in more specific aspects, $R^1$ is —CH$_3$. In some aspects, $R^2$ is selected from the group consisting of —C(O)O—, —C(O)N—, —CH$_2$O—, —O—, —(CH$_2$)$_z$—, and in more specific aspects $R^2$ is —C(O)O—. In some aspects, $R^3$ is a linear, branched, or cyclic fluorocarbon group having 1-24 carbon atoms, 2-48 fluorine atoms, and 0-48 hydrogen atoms. In more specific aspects, $R^3$ is —(CR$^4$R$^5$)$_q$CR$^6$R$^7$R$^8$, where $R^4$, $R^5$, $R^6$, $R^7$, and $R^8$, are independently selected from H and F, provided that at least two of $R^4$, $R^5$, $R^6$, $R^7$, and $R^8$, are F, and wherein $q$ is in the range of 0 to 20. In more specific aspects, $R^3$ is a linear, branched, or cyclic fluorocarbon group of the formula —(CR$^4$R$^5$)$_q$CR$^6$R$^7$R$^8$ having 1-12 carbon atoms, 2-24 fluorine atoms, and 0-24 hydrogen atoms.

Exemplary monomers of formula II include fluorinated acrylates. In fluorinated acrylates the $R^2$ of formula II is —C(O)O—. Exemplary fluorinated acrylates of the invention are selected from the group consisting of 2,2,2-trifluoroethyl (meth)acrylate, 2,2,3,3,3-pentafluoropropyl(meth)acrylate, 1,1,1,3,3,3-hexafluoroisopropyl(meth)acrylate, and 2,2,3,3,4,4,5,5-octafluoropentyl(meth)acrylate.

Fluorinated acrylates are commercially available from Sigma-Aldrich and DuPont under the tradename Zonyl™.

Other contemplated monomers that can provide non-backbone fluorine atoms to the fluoropolymer include certain fluorinated oxy-alkenes according to formula III:

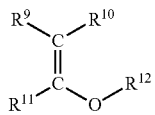

III

Wherein $R^9$, $R^{10}$, and $R^{11}$ is independently selected from H and F, and $R^{12}$ is a fluorocarbon group, provided that the number of fluorine atoms in $R^{12}$ is greater than any total amount of fluorine atoms present in $R^9$, $R^{10}$, and $R^{11}$.

Exemplary fluorinated oxy-alkenes according to formula III include 1,1,2-trifluoro-2-pentafluoroethyloxy-ethene (i.e., perfluoroethylvinyl ether; Dupont), 2-{1-[difluoro(trifluoroethenyl)oxy]methyl}-1,2,2,2-tetrafluoroethoxy]-1,1,2,2-tetrafluoro ethanesulfonylfluoride (i.e., perfluoro-2-(2-fluorosulfonylethoxy) propyl vinyl ether; Dupont), and 3-1-difluoro (trifluoroethenyl)oxy methyl-1,2,2,2,-tetrafluoroethoxy-2,2,3,3,-tetrafluoropropanoic acid methyl ester (i.e., ester vinyl ether; Dupont).

Other contemplated monomers that can provide non-backbone fluorine atoms to the fluoropolymer include certain fluorinated epoxides according to formula IV:

IV wherein one or more of $R^{13}$, $R^{14}$, $R^{15}$, and/or $R^{16}$ is a fluorocarbon group and those $R^{13}$, $R^{14}$, $R^{15}$, and/or $R^{16}$ that is/are not fluorocarbon group(s) are either H or F provided that the number of fluorine atoms present in the fluorocarbon group(s) is greater than any number of fluorine atom(s) if one or more of $R^{13}$, $R^{14}$, $R^{15}$, and/or $R^{16}$ is F.

Exemplary fluorinated epoxides according to formula IV include hexafluoroisobutylene epoxide (2,2-bis(trifluoromethyl) oxirane; Dupont) and 2-(heptafluoroisopropyl)methyl oxirane (see, for example, Církva, V. et al, (2003) *Journal of Fluorine Chemistry*, 121:101-104).

Optionally, the fluoropolymer can be prepared using combinations of different fluoromonomers that provide non-backbone fluorine atoms to the fluoropolymer. For example, combinations of different monomers of formula I can be used, such as those having different fluorocarbon groups.

In some cases, the fluoropolymer can be described in terms of the weight percentage of the fluorinated monomers (or combination of fluorinated monomers) in the fluoropolymer. In some aspects, the fluorinated monomers that provide non-backbone fluorine atoms are present in the fluoropolymer in an amount of less than about 50% wt of the fluoropolymer. In more specific aspects the fluorinated monomers that provide non-backbone fluorine atoms are present in the fluoropolymer in an amount in the range of from about 1% wt to about 40% wt, from about 2.5% wt to about 35% wt, from about 5% wt to about 30% wt, or from about 7.5% wt to about 25% wt.

In some cases, the fluoropolymer can be described in terms of the molar quantity of non-backbone fluorine atoms per weight of the fluoropolymer. In some aspects, the non-backbone fluorine atoms are present in the fluoropolymer in an amount of less than 11 mmol/gram of the fluoropolymer. In more specific aspects the non-backbone fluorine atoms are present in the fluoropolymer in an amount in the range of from about 0.2 mmol/gram to about 9 mmol/gram, from about 0.5 mmol/gram to about 8 mmol/gram, from about 1 mmol/gram to about 6.5 mmol/gram, or from about 1.5 mmol/gram to about 5.5 mmol/gram.

The particular fluoromonomer amount in the fluoropolymer can be chosen based on the types and amounts of materials used in the composition. For example, if the composition includes as the predominant polymeric material the fluoropolymer, it may be sufficient to use fluoropolymers having lower fluoromonomer loads, such as in the range of from about 1% wt to about 20% wt (or from about 0.2 mmol/gram to about 4.5 mmol/gram), or from about 2% wt to about 15% wt (or from about 0.4 mmol/gram to about 3.25 mmol/gram). However, if the fluoropolymer is used in the composition with one or more other non-fluorinated polymers, it may be desirable to use fluoropolymers having higher fluoromonomer loads, such as in the range of from about 10% wt to about 40% wt (or from about 2.25 mmol/gram to about 9 mmol/gram), or from about 15% wt to about 35% wt (or from about 3.25 mmol/gram to about 8 mmol/gram).

Optionally, the fluoropolymers of the invention can include one or more fluorinated monomer(s) that provides one or more polymeric backbone fluorine atoms per monomeric unit. If included, these monomer types are used in the fluoropolymer in an amount which provides backbone fluorines in a quantity that is less than the non-backbone fluorine atoms of the fluoropolymer. Examples of fluorinated monomers that provide backbone fluorines include tetrafluoroethylene, trifluoroethylene, 1,1-difluoroethylene (vinylidene fluoride), 1,2 difluoroethylene, and monofluoroethylene.

Optionally, fluorinated monomers can be used that provide a combination of polymeric backbone fluorine atoms and non-backbone fluorine atoms. If included in the fluoropolymers of the invention, these monomer types can optionally be used to provide backbone fluorines in an amount less than the non-backbone fluorine atoms of the fluoropolymer. Examples of fluorinated monomers that provide both backbone and non-backbone fluorine atoms include hexafluoropropylene; 1,2,3,3,3-pentafluoropropylene; 3,3,3-trifluoropropene-1; and 2,2,3-trifluoro-3-trifluoromethoxy-oxirane.

In one embodiment. the fluoropolymers include a non-fluorinated hydrophilic monomer. The fluoropolymers can be prepared using one type of non-fluorinated hydrophilic monomer, or two or more different types of non-fluorinated hydrophilic monomers. The one or more non-fluorinated hydrophilic monomer(s) can be selected from any suitable non-fluorinated hydrophilic monomer which can be copolymerized with a fluorinated monomer, such as those described herein, to provide a fluoropolymer of the invention.

Exemplary non-fluorinated hydrophilic monomers include those selected from methyl acrylate, methyl methacrylate, hydroxyethyl methacrylate, hydroxyethyl acrylate, hydroxypropyl acrylate, hydroxypropyl methacrylate, hydroxypropyl methacrylamide, acrylic acid, methacrylic acid, glyceryl acrylate, glyceryl methacrylate, methacrylamide, acrylamide, methacrylic acid, vinyl acetate, vinyl alcohol, methyl vinyl ether, (meth)-acrylamide derivatives, such as alkyl (meth)acrylamide and aminoalkyl(meth)acrylamide, such as aminopropylmethacrylamide and dimethylaminopropylmethacrylamide, and vinyl pyrrolidone.

In one composition the fluoropolymer includes vinyl pyrrolidone. Vinyl pyrrolidone has an absorption spectrum in the region of about 200-280 nm (e.g., at 254 nm) and the UV treatment of this monomer (with the fluoropolymer) can lead to radical formation. (See, for example, Lopérgolo, et al. (2003) *Polymer* 44: 6217-6222). As such, radicals formed on a vinyl pyrrolidone-containing fluoropolymer can undergo recombination, resulting in the crosslinking of fluoropolymers via activated pyrrolidone groups.

Therefore, if vinyl pyrrolidone is present in the fluoropolymer, or if vinyl pyrrolidone is present in a non-fluorinated polymer in the composition, such as a secondary polymer, it is not required than the composition include another photoactivatable group, such as aryl ketone-type photogroups described herein. However, if it desired to increase the photosensitivity of the composition, the fluoropolymer, and/or a secondary polymer, can include vinyl pyrrolidone as well as another photoactivatable group.

In some aspects, the non-fluorinated hydrophilic monomer is present in the fluoropolymer in an amount by weight greater than the fluorinated monomer (i.e., the non-fluorinated hydrophilic monomer is present at least greater than 50% wt). In more specific aspects, the non-fluorinated hydrophilic monomer is present in the fluoropolymer in an amount in the range of from about 60% wt to about 99% wt, from about 65% wt to about 97.5% wt, from about 70% wt to about 95% wt, or from about 75% wt to about 92.5% wt.

The amount of the non-fluorinated hydrophilic monomer can be chosen based on the types and amounts of materials used in the composition. For example, if the composition includes as the predominant polymeric material the fluoropolymer, it may be desirable to use a fluoropolymer(s) having a higher non-fluorinated hydrophilic monomer loads, such as in the range of from about 80% wt to about 99% wt, or from about 85% wt to about 98% wt. However, if the fluoropolymer is used in the composition with one or more other non-fluorinated polymers, it may be desirable to use fluoropolymers having lower non-fluorinated hydrophilic monomer loads, such as in the range of from about 60% wt to about 90% wt, or from about 65% wt to about 85% wt, which thereby increases the fluoromonomer load in the fluoropolymer.

Optionally, the fluoropolymer can be prepared with a hydrophilic monomer that provides a pendent charged group to the fluoropolymer. For example, a monomer providing a negatively charged group such as sulfonate or phosphonate can optionally be in the fluoropolymer. An exemplary sulfonate-containing monomer is 2-acrylamido 2-methyl propane sulfonate (AMPS). As another option, a monomer that provides a positively charged group such as quaternary ammonium, quaternary phosphonium, and ternary sulfonium groups can be used in the fluoropolymer. An exemplary sulfonate-containing monomer is (3-acrylamidopropyl)-trimethylammonium chloride (APTAC; Simga-Aldrich Corp., St. Louis, Mo.).

In some aspects, the fluoropolymer can include a non-sulfonated or non-phosphonated hydrophilic monomer, such as n-vinyl pyrrolidone or acrylamide, and a sulfonated or phosphonated hydrophilic monomer, such as AMPS. The sulfonated or phosphonated hydrophilic monomer can be used in amount less than that of the non-sulfonated or non-phosphonated hydrophilic monomer (non-fluorinated hydrophilic monomer) in the fluoropolymer. For example, the fluoropolymer can include a sulfonated or phosphonated hydrophilic monomer in an amount of about 50% wt of the fluoropolymer or less, such as in the range of from about 0.5% wt to about 10% wt., and the non-sulfonated or non-phosphonated hydrophilic monomer is used in an amount of about 50% wt or greater.

The total amount of non-fluorinated hydrophilic polymer in the fluoropolymer can include the sulfonated or phosphonated hydrophilic monomer and the non-sulfonated or non-phosphonated hydrophilic monomers (non-fluorinated hydrophilic monomer) in the fluoropolymer.

Compositions of the invention can also include a polymer and/or component having a photoreactive group. Generally, the photoreactive group can be treated with actinic radiation to activate the photogroup to a radical species which is then able to react with a target component and promote stabilization of the fluoropolymer in the treated composition. For example, a coating composition including the fluoropolymer and photogroup can be treated with UV radiation to cause covalent crosslinking of the fluoropolymer in the composition, and/or covalent immobilization of the fluoropolymer to a device surface. The covalent bonding as caused by activation of the photoreactive group can improve the stability of the coating components and can provide a coating with improved durability.

A "latent photoreactive group," as used herein, refers to a chemical group that responds to applied electromagnetic energy in order to undergo active specie generation, resulting in covalent bonding to an adjacent chemical structure (via an abstractable hydrogen). "Photoreactive" or "latent" refers to those groups that are responsive to the electromagnetic energy but that have not yet been activated to undergo covalent bonding, whereas "photoreacted" or "reacted" refers to those groups that have been activated by electromagnetic energy and have undergone covalent bonding to a target moiety.

Latent reactive groups can be sufficiently stable to be stored under conditions in which they retain such properties. See, for example, U.S. Pat. No. 5,002,582 (Guire et al.). Latent photoreactive groups can be chosen that are responsive to various portions of the electromagnetic spectrum. Latent reactive groups responsive to ultraviolet and visible portions of the spectrum can be particularly useful.

Photoreactive species responds to a specific applied external ultraviolet or visible light source to undergo active specie generation with resultant covalent bonding to an adjacent chemical structure, for example, as provided by the same or a different molecule. Photoreactive species are those groups of atoms in a molecule that retain their covalent bonds unchanged under conditions of storage but that, upon activation by a specific applied external ultraviolet or visible light source form covalent bonds with other molecules. Photoreactive species generate active species such as free radicals and particularly nitrenes, carbenes, and excited states of ketones, upon absorption of electromagnetic energy.

A UV activated photogroup can undergo covalent bonding to a target moiety. The target moiety can be an atom of any one or more compound(s) or one or more of material(s) of an article made using the fluoropolymer, or associated with the fluoropolymer. Exemplary target moieties include, but are not limited to, the fluoropolymer, another (secondary) polymer in mixture with the fluoropolymer, another polymer that is not in mixture with the fluoropolymer, or material of a device surface, or even a biomolecule. Covalent bonding with the target moiety can result in fluoropolymer-fluoropolymer cross-linking in a polymeric matrix, fluoropolymer-secondary polymer cross-linking in a polymeric matrix, fluoropolymer bonding to another polymer that is not in mixture with the fluoropolymer, such as in an adjacent coated layer, or fluoropolymer bonding to a structural material of a medical device, such as a thermoplastic material. In some cases, the excited state of UV activated photogroup can insert into a carbon-hydrogen bond by abstraction of a hydrogen atom from the target moiety, thus creating a radical pair. Subsequent collapse of the radical pair leads to formation of a new carbon-carbon bond, and covalent bonding of the fluoropolymer to the target moiety.

Exemplary latent photoreactive groups are aryl ketones, such as acetophenone, benzophenone, anthraquinone, anthrone, and anthrone-like heterocycles (for example, heterocyclic analogs of anthrone such as those having nitrogen, oxygen, or sulfur in the 10-position), or their substituted (for example, ring substituted) derivatives.

Aryl ketones are photoreactive moieties, since they are capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (for example, carbon-hydrogen) is not available for bonding, the ultraviolet light-induced excitation of the benzophenone group is reversible and the molecule returns to ground state energy level upon removal of the energy source. Photoactivatable aryl ketones such as benzophenone and acetophenone are of particular importance inasmuch as these groups are subject to multiple reactivation in water and hence provide increased bonding efficiency.

In one embodiment, a photoreactive group is pendent from a monomer in the fluoropolymer. The photoreactive group can be introduced into the fluoropolymer according to any one of various methods. For example, in one mode of practice a monomer is obtained or prepared having a photoreactive group. The monomer is then polymerized along with a fluorinated monomer and a non-fluorinated hydrophilic monomer to provide the fluoropolymer with a pendent latent reactive photogroup.

Exemplary monomers with photoreactive groups that can be incorporated into the fluoropolymer include those based on acrylamide and methacrylamide. One exemplary methacrylamide-based monomer with a pendent photoreactive groups is N-[3-(4-benzoylbenzamido)propyl]methacrylamide (BBA-APMA), the synthesis which is described in Examples 1-3 of U.S. Pat. No. 5,858,653 (Duran et al.) Another exemplary methacrylamide-based monomer with a pendent photoreactive group is N-[3-(7-methyl-9-oxothioxanthene-3-carboxiamido)propyl]methacrylamide (MTA-APMA), the synthesis which is described in Examples 1-2 of U.S. Pat. No. 6,156,345 (Chudzik et al.)

For fluoropolymers including a monomer with a pendent photoreactive group, the fluoropolymers are synthesized to have at least one photoreactive group per polymer. More typically, the fluoropolymer is prepared to provide a loading of the photoreactive group on the fluoropolymer in the range of about 0.01 mmol/g to about 1 mmol/g (mmol photoreactive group per gram of fluoropolymer), and more specifically in the range of about 0.1 mmol/g to about 0.5 mmol/g.

Alternatively, in another mode of practice, the fluoropolymer is prepared with a monomer having a group (e.g., a primary amine group) that can specifically react with a compound that has a photoreactive group and a corresponding reactive group. For example, the fluoropolymer can be prepared with a monomer that presents a pendent amine group, such as N-(3-aminopropyl)methacrylamide, following its synthesis. An amount of monomer can be chosen to provide a desired level of loading of photoreactive groups following synthesis. Following its preparation, the fluoropolymer is then reacted with a photoreactive group-containing compound under conditions to promote covalent bonding of the photogroup to the amine group on the fluoropolymer. An example of an amine reactive photoreactive group-containing compound is 4-benzoylbenzoyl chloride, which can be reacted with a primary amine group pendent from the fluoropolymer under Schotten-Baumann conditions (see, for example, Example 2 of U.S. Pat. No. 5,563,056 (Swan et al.))

Polymerization of the fluorinated monomer, hydrophilic monomer, and optionally a monomer having a pendent photoreactive group can be carried out under standard reaction conditions. One or more solvents can be chosen for the polymerization composition based on the solubility profiles of the various monomers. Exemplary solvents for polymerization include water and organic solvents. In one mode of practice polymerization is carried out in a composition using DMSO as the solvent. In another mode of practice, polymerization is carried out in a composition using water, THF and ethanol. Total monomer concentration in the polymerization composition typically ranges from about 1% wt to about 20% wt, and more specifically from about 5% wt to about 10% wt.

In one mode of practice, free radical polymerization is carried out in a composition containing the desired monomers.

For fluoropolymers prepared to have a pendent photoreactive group, polymerization initiator system can be based on redox components. Exemplary redox polymerization initiators include ammonium persulfate (APS), 2-azobis(isobutyro-nitrile), potassium persulfate, and organic peroxides, including hydroperoxides, for example alkyl hydroperoxides, such as para-menthane, t-butyl hydroperoxide, and t-butyl perbenzoate. Co-initiators, such as tetramethylethylenediamine (TEMED) can be used.

The polymerization composition can be deoxygenated by sparging with an inert gas such as helium or nitrogen. Polymerization can be carried out at temperatures in the range of from about 25° C. to about 80° C.

After polymerization is complete, the fluoropolymer can be isolated by addition of a non-solvent or through dialysis in water or other polar solvents.

Alternatively, the invention provides a composition wherein the photoreactive group is present on a non-polymeric compound, such as a crosslinking compound. The photogroup(s) in the crosslinking component can crosslink polymeric material together in the composition. For example, the crosslinked polymeric material can be crosslinked fluoropolymers, or a fluoropolymer crosslinked to one or more other (secondary, tertiary, etc.) polymer(s) in the composition. Depending on how the fluoropolymer-containing composition is used, the crosslinking component can also bond the fluoropolymer to a material of a device surface. The bonding can improve coating properties, such as durability.

An example of a simple crosslinking component is benzophenone, which has solubility in solvents such as tetrahydrofuran and ethanol.

In some aspects, the composition includes a crosslinking component that includes two or more photoreactive groups. In some aspects, the crosslinking component agent is ionic and soluble in an aqueous composition. An exemplary ionic photoactivatable cross-linking agent is a compound of formula V:

where Q is a radical containing at least one acidic group, basic group, or a salt of an acidic group or basic group. $X_2$ and $X_3$ are each independently a radical containing a latent photoreactive group.

The photoreactive groups can be the same as those described herein. Spacers can also be part of $X_2$ or $X_3$ along with the latent photoreactive group. In some embodiments, the latent photoreactive group includes an aryl ketone or a quinone. The radical Q in formula V provides the desired water solubility for the ionic photoactivatable cross-linking agent.

In some embodiments of formula V, Q is a radical containing at least one acidic group or salt thereof. Such a photoactivatable cross-linking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic cross-linking agent includes a sulfonic acid or sulfonate group. Suitable counter ions include alkali, alkaline earths metals, ammonium, protonated amines, and the like.

For example, a compound of formula V can have a radical Q that contains a sulfonic acid or sulfonate group; $X_2$ and $X_3$ can contain photoreactive groups such as aryl ketones. Such compounds include 4,5-bis(4-benzoylphenylmethyleneoxy) benzene-1,3-disulfonic acid or salt; 2,5-bis(4-benzoylphenylmethyleneoxy)benzene-1,4-disulfonic acid or salt; 2,5-bis (4-benzoylmethyleneoxy)benzene-1-sulfonic acid or salt; N,N-bis[2-(4-benzoylbenzyloxy) ethyl]-2-aminoethanesulfonic acid or salt, and the like. See U.S. Pat. No. 6,278,018 (Swan). The counter ion of the salt can be, for example, ammonium or an alkali metal such as sodium, potassium, or lithium.

In other embodiments of formula V, Q can be a radical that contains a basic group or a salt thereof Such Q radicals can include, for example, an ammonium, a phosphonium, or a sulfonium group. The group can be neutral or positively charged, depending upon the pH of the coating composition. In some embodiments, the radical Q includes an ammonium group. Suitable counter ions include, for example, carboxylates, halides, sulfate, and phosphate.

For example, compounds of formula V can have a Q radical that contains an ammonium group; $X_2$ and $X_3$ can contain photoreactive groups that include aryl ketones. Such photoactivatable cross-linking agents include ethylenebis(4-benzoylbenzyldi-methylammonium) salt; hexamethylenebis(4-benzoylbenzyldimethylammonium) salt; 1,4-bis(4-benzoylbenzyl)-1,4-dimethylpiperazinediium) salt, bis(4-benzoylbenzyl)hexa-methylenetetraaminediammonium salt, bis[2-(4-benzoylbenzyldimethylammonio)ethyl]-4-benzoylbenzylmethylammonium salt; 4,4-bis(4-benzoylbenzyl)morpholinium salt; ethylenebis[(2-(4-benzoylbenzyldimethylammonio)ethyl)-4-benzeylbenzylmethyl-ammonium]salt; and 1,1,4,4-tetrakis(4-benzoylbenzyl)piperzinediammonium salt. See U.S. Pat. No. 5,714,360 (Swan, et al). The counter ion is typically a carboxylate ion or a halide. On one embodiment, the halide is bromide.

In other aspects a non-ionic photoactivatable cross-linking agent can be used. In one embodiment, the non-ionic photoactivatable cross-linking agent has the formula $XR^{17}R^{18}R^{19}R^{20}$, where X is a chemical backbone, and $R^{17}$, $R^{18}$, $R^{19}$, and $R^{20}$ are radicals that include a latent photoreactive group. Exemplary non-ionic cross-linking agents are described, for example, in U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

Some suitable cross-linking agents are those formed by a mixture of the chemical backbone molecule (such as pentaerythritol) and an excess of a derivative of the photoreactive group (such as 4-bromomethylbenzophenone). An exemplary product is tetrakis(4-benzoylbenzyl ether) of pentaerythritol (tetrakis(4-benzoylphenylmethoxy-methyl) methane). See U.S. Pat. Nos. 5,414,075 and 5,637,460 (Swan et al).

If included in a composition, the cross-linking agent can be at a concentration that can improve the properties of the polymeric matrix (e.g., coating) formed using the composition. A photo-crosslinking agent can be used at a concentration in the composition to affect bonding of polymeric material within the composition, or to a device surface, or both, as desired.

The amount of crosslinking agent can be described in terms of the weight by volume in the composition, or the weight of the crosslinker per weight of total polymeric material. In some modes of practice, the composition includes a crosslinking reagent in an amount in the range of from about 0.2 mg/mL to about 5 mg/mL. In some modes of practice, the composition includes an amount of fluoropolymer in the range of from about 30 to about 100 mg/mL.

In some embodiments, the coating is formed by a process that includes disposing a nonpolymeric compound including photoreactive groups, or a non-fluorinated polymer including pendent photoreactive groups, on the device prior to disposing the composition that includes the fluorinated polymer.

For example, a photoreactive cross-linking agent, or a non-fluorinated photopolymer, can be disposed on the device surface (or a primer layer on the surface), followed by disposing a coating composition that includes the fluoropolymer. Following irradiation, covalent bonds are formed between the device surface, the crosslinking agent or non-fluorinated polymer, and the fluoropolymer.

In some aspect, the composition includes the fluoropolymer and one or more other polymers. Generally, the one or more other polymers are partially or entirely composed of hydrophilic monomers, which can be non-fluorinated.

For example, in one aspect the composition includes the fluoropolymer and a second hydrophilic polymer. The second hydrophilic polymer can be a homopolymer or a copolymer prepared from methyl acrylate, methyl methacrylate, hydroxyethyl methacrylate, hydroxyethyl acrylate, hydroxypropyl acrylate, hydroxypropyl methacrylate, hydroxypropyl methacrylamide, acrylic acid, methacrylic acid, glyceryl acrylate, glyceryl methacrylate, methacrylamide, acrylamide, methacrylic acid, vinyl acetate, vinyl alcohol, methyl vinyl ether, (meth)acrylamide derivatives, such as alkyl (meth)acrylamide and aminoalkyl(meth)acrylamide, such as aminopropylmethacrylamide and dimethylaminopropylmethacrylamide, and vinyl pyrrolidone or combinations of any two or more of these monomers.

In one embodiment, the composition includes a second polymer that is a vinyl pyrrolidone homopolymer. In another embodiment the composition includes a second polymer that is a copolymer of vinyl pyrrolidone and an acrylamide monomer.

In another embodiment, the composition includes a second polymer that is hydrophilic and that includes a pendent photoreactive group. In this embodiment, the second hydrophilic polymer can be a homopolymer or a copolymer that includes any one or combinations of hydrophilic monomers as described herein, in addition to a monomer the provides a pendent photoreactive group, such as BBA-APMA or MTA-APMA. The amount of photoreactive group present in the composition containing a blend including the fluoropolymer and a second hydrophilic polymer with pendent photoreactive groups can be described in terms of photoreactive group per total polymeric material (mmol/g).

Compositions of the invention which are formed using the fluoropolymer of the invention, or the fluoropolymer of the invention in combination with one or more additional polymers (e.g., second, third, etc.) can be described in terms of the overall amount of polymeric material in the composition (mg/mL).

In some modes of practice, the fluoropolymer-containing composition is used for coating an implantable medical device and has a concentration of polymeric material in the range of about 5 mg/mL to about 100 mg/mL, or more specifically about 10 mg/mL to about 60 mg/mL. In some aspects, if more than one polymer is present in the first coating composition, the combined amount of polymeric materials can be in the ranges as described.

Compositions, e.g., coating compositions, of the invention can include the fluoropolymer of the invention, and optionally one or more other polymeric materials, that are suspended or dissolved in a solvent. Optionally, other materials, such as other non-polymeric materials, can be included in the composition.

The composition of the invention can also include an imaging material. The imaging material can be present in a coating formed from the composition, or in a polymeric matrix of a different form. The imaging material can facilitate detection of the device once inserted or implanted in a patient.

One class of imaging materials are colorants. A coating formed from a composition including a colorant can be useful for monitoring the insertion of the article into a patient. The colorant(s) can provide a visual cue to the end user to indicate where the coating composition is located along the coated article (in other words, what portions of the device surface are coated). The presence of a coating on a device surface is often determined by tactile means, meaning that the user can feel the portions of the device that are provided with a lubricious coating. A coating with a colorant can allow the user to visually determine the coated portions of the device, as compared to the more tactile methods. Being able to visually determine the coated portions of the device can improve also improve safety by reducing the handling of the device, which minimizes contamination by microorganisms. A coating can be formed with a colorant in one or more particular portion(s) of the coating, or in the entire coating.

Example of colorants that can be used in the preparation of coatings of the present invention include, but are not limited to, FD&C and D&C lakes, titanium dioxide, magnesium carbonate, talc, pyrogenic silica, iron oxides, channel black, insoluble dyes, natural colorants (such as riboflavin, carmine 40, curcumin, and annatto), dyes approved for ingestion by the U.S. Federal Drug Administration, or a combination of any of these. Colorants used in making coating dispersions for coating tablets, food, confectionery forms, agricultural seeds, and the like can be used in the coatings of the present invention.

Other exemplary imaging materials include paramagnetic materials, such as nanoparticular iron oxide, Gd, or Mn, radioisotopes, and radio-opaque materials. The degree of radiopacity contrast can be altered by controlling the concentration of the radio-opaque materials within the coating. Common radio-opaque materials include barium sulfate, bismuth subcarbonate, and zirconium dioxide. Other radio opaque materials include cadmium, tungsten, gold, tantalum, bismuth, platinum, iridium, and rhodium.

Bioactive agents can optionally be included in the composition, or in the coating including the fluorinated polymer. A coating formed from such a composition can provide a bioactive agent at the location of insertion or implantation, and can enhance use of the device, prevent infection, or treat a pre-existing condition.

Exemplary bioactive agents include, but are not limited to, antibiotics, anit-microbials, anti-inflammatory agents, anti-proliferative agents, immunomodulatory agents, anti-mitotics, and anesthetics. Particularly useful bioactive agents of these classes include macrolide antibiotics such as rapamycin (triene macrolide antibiotic) and rapamycin analogs; immunomodulatory agents such as ABT-578; anti-mitotics including taxoid drugs such as paclitaxel and docetaxel; anti-inflammatory agents such as dexamethasone and betamethasone; and anesthetics such as lidocaine or tetracaine.

In some aspects the fluoropolymer-containing composition is used to coat the surface of a medical device to provide a lubricious coating. The coatings are particularly useful for medical articles that can be inserted into and moved within the body.

The coated medical article or device can be any that is introduced temporarily or permanently into a mammal for the prophylaxis or treatment of a medical condition. These articles or devices include any that are introduced subcutaneously, percutaneously or surgically to move or rest within an organ, tissue, or lumen of an organ. In some aspects the coated medical article is inserted into a portion or portions of the urogenital system, such as the urethra. In some aspects the coated medical article is inserted into a portion or portions of the cardiovascular system, such as an artery, vein, ventricle, or atria of the heart.

Exemplary medical articles that can be provided with a coating including the fluoropolymer of the invention include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septal defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors including glucose sensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

The coating containing the fluoropolymer can be formed on any biomaterial surface. Commonly used biomaterial surfaces include plastic materials and metals. Exemplary plastic materials include polyvinylchloride (PVC), polytetrafluoroethylene (PTFE), polyethersulfone (PES), polysulfone (PS), polypropylene polyethylene, (PE), polyurethane (PU), polyetherimide (PEI), polycarbonate (PC), and polyetheretherketone (PEEK).

Metals that can be used in medical articles include platinum, gold, or tungsten, as well as other metals such as rhenium, palladium, rhodium, ruthenium, titanium, nickel, and alloys of these metals, such as stainless steel, titanium/nickel, nitinol alloys, and platinum/iridium alloys. These metals, including other alloys or combinations, can serve as suitable substrates for disposing the coating composition.

Prior to disposing the coating composition on the surface of the article, the article can be cleaned using any suitable technique.

Although many devices or articles are constructed from substantially all metal materials, such as alloys, some may be constructed from both non-metal and metal materials, where at least a portion of the surface of the device is metal. The metal surface may be a thin surface layer. Such surfaces can be formed by any method including sputter coating metal onto all or portions of the surface of the device.

To exemplify the benefits that the coatings of the present invention provide to medical devices, a fluoropolymer coating on the surfaces of a cardiac catheter is discussed.

A cardiovascular catheter is typically a long cylindrically-shaped device made of a plastic material that is inserted into the vasculature of a patent, with the distal end of the catheter advanced through the vasculature to a target location. For example, a catheter is inserted into femoral artery in the groin or the radial artery in the wrist, and advanced into the chambers of the heart or into the coronary arteries. Typically, a guidewire is used to push the catheter to a target location in the body.

A fluoropolymer-based coating on at least the external wall of the catheter can improve movement in the vasculature by reducing the frictional forces during the insertion process. While the fluoropolymer coating of the invention is able to become hydrated, which increases its lubricity (i.e., "wet lubricity") the coating also benefits from the fluorine chemistries with provide a "dry lubricity." The nature of the polymeric materials can prevent excessive hydrophilic swelling of the coated surface, which is beneficial because the outer diameter of the device can be controlled, and the coating does not suffer from a decrease in lubricity as otherwise caused by water being squeezed out of the coating which may be observed in highly hydrophilic coatings. As such, movement of the catheter having the fluorinated polymer coating of the invention can therefore be significantly enhanced during insertion and withdrawal of the catheter from the body.

As used herein, the term "layer" or "coated layer" will refer to a layer of one or more coated materials of sufficient dimensions (for example, thickness and area) for its intended use over the entire, or less than the entire, portion of an article surface. Therefore, a "coating" as described herein can include one or more "coated layers," each coated layer including one or more coating components. In the least, a coating includes the fluoropolymer of the invention. If the coating includes two or more layers, materials from one coated layer may migrate into adjacent coated layers, depending on the components of a particular coating composition, including the solvent or solution, and dissolved or suspended coating compounds. Therefore, to a certain extent, a coated layer may contain components from an adjacent coated layer.

One or more additional optional coated layers can be included in the coating. Typically, the fluoropolymer is located in the coating so that it contacts a body fluid or tissue, and therefore it is generally located at the outermost (e.g. top) portion of the coating. If one or more additional optional coated layers are present in the coating, the additional layer(s) are typically located between the fluoropolymer and the surface of the device. Therefore, when referring to the step of disposing a fluoropolymer-containing coating composition on a surface, the surface may be that of the device itself, or the surface of the device with one or more optional coated layers. For purposes of discussion, if an optional layer(s) is present, it can be referred to as an intermediate layer, and can also be described relative to the material of the device surface (e.g., "closer/proximal to the surface," "further/distal from the surface," "in contact with the surface," etc.).

An optional coated layer can facilitate formation of the fluoropolymer on the article. For example, the fluoropolymer can be disposed on a medical device precoated with a non-polymeric silane compound. Exemplary, silane precoatings are described in U.S. Pat. No. 6,706,408 (Jelle).

These types of optional base coated layers can be particularly useful for providing a surface that can be reacted with a latent reactive group, such as a photoreactive group, that can be included in a coating composition or present in the fluoropolymer.

A step in the coating process involves disposing a coating composition including the fluoropolymer on a surface of a device. The coating composition can optionally include one or more other polymers and/or a crosslinking compound. The applied composition is then treated to affect the photoreactive groups, which promotes formation of the coating.

The coating process can be carried out at a temperature suitable to provide a desired coating to the surface, or a portion of the surface, of the article. The coating process can be carried out at a temperature in the range of about 10° C. to about 50° C., and alternatively at a temperature in the range of from about 15° C. to about 25° C. However, the actual coating temperature can be chosen based on aspects of the coating composition, including the liquid used to dissolve or suspend the polymeric material, the polymeric material, and also the method used to dispose the coating composition on the surface of the article or device.

The coating composition can be applied to the surface of a device using any suitable technique. For example, the coating composition can be dipped, sprayed, sponged, or brushed on a device to form a layer, and then dried. In some modes of practice, the coating composition can be applied by dip-coating. Optionally, the process can be repeated to provide a coating having multiple coated layers (e.g., multiple layers formed from the fluoropolymer-containing coating composition). The suitability of the coating composition for use with a particular medical article, and in turn, the suitability of the application technique, can be evaluated by those skilled in the art, given the present description.

A typical dip-coating procedure involves immersing the article to be coated in the coating composition, dwelling the object in the composition for a period of time (a standard time is generally less than about 30 seconds, and can even be less that 10 seconds in many cases), and then removing the article from the composition. After the article has been dip-coated in the coating solution, it is removed and dried. Drying can be carried out using any suitable method, including air-drying the dip coated article. Times up to 30 minutes can be sufficient to dry the coated article although shorter times may be also sufficient.

A step of irradiating can be performed to activate the latent photoreactive groups in the applied coating materials. For example, the coating can be treated with UV irradiation following the step of disposing the coating composition that includes the fluorinated polymer. The step of activating can be performed before and/or after the coated material dries on the surface of the device.

Generally, the step of irradiating can be performed by subjecting the photoreactive groups to actinic radiation in an amount that promotes activation of the photoreactive group and bonding to a target moiety. The step of irradiating can be performed after the coating composition is disposed.

Actinic radiation can be provided by any suitable light source that promotes activation of the photoreactive groups. Light sources (such as those available from Dymax Corp.) provide UV irradiation in the range of about 190 nm to 360 nm. A suitable dose of radiation is in the range of from about 0.5 mW/cm$^2$ to about 2.0 mW/cm$^2$.

In some aspects, it may be desirable to use filters in connection with the step of activating the photoreactive groups. The use of filters can be beneficial from the standpoint that they can selectively minimize the amount of radiation of a particular wavelength or wavelengths that are provided to the coating during the activation process. This can be beneficial if one or more components of the coating are sensitive to radiation of a particular wavelength(s), and that may degrade or decompose upon exposure. Typically, filters are identified by the wavelength of light that is permitted to pass through the filter. Two illustrative types of filters that can be used in connection with the invention are cut-off filters and band pass filters. Generally, cut-off filters are categorized by a cut-off transmittance, where the light transmittance is approximately 25% of the maximum transmittance. For band pass filters, a range of wavelength is identified for the filter, and the center wavelength is the midpoint of wavelength allowed through; at midpoint, the transmittance is approximately half of the maximum transmittance allowed through the filter. Thus, in one embodiment utilizing a band pass filter, for example, an Edmund 407 nm filter, the filter can be chosen that has a maximum UV transmittance at its center wavelength of 407 nm. In another embodiment, a band pass filter having a maximum transmittance at 500 nm is used.

The coating process can be carried out to provide a coating having a desired thickness, and that is durable and has excellent lubricious properties. The process can be carried out to provide a coating thickness that is suitable for the device that is being coating and the method that the coated device is being used for.

The coating including the fluoropolymer can also be described in terms of thickness. It is understood that a very thin coated layer (e.g., such as about 0.5 µm dried) can be formed on the surface device, as well as substantially thick coatings (e.g., such as about 5 mm dried). Thicker coatings can be formed by sequentially applying a coating composition including the fluoropolymer. The coating thickness can also be controlled by varying the liquid in the composition, as well as by changing the concentration of the fluoropolymer in solution. For use on an implantable medical device, such as a catheter, the coating thickness can fall within a targeted range of thickness.

Since the fluoropolymer coating may experience an amount of swelling upon contact with water, the thickness can be described in terms of the coating when it is in a dried state, as well as when it is fully hydrated. For example, in some aspects the coating has a thickness in a dried state of from about 0.25 µm to about 10 µm, or more specifically in the range of from about 0.5 µm to about 5 µm. In a fully hydrated state the coating can have a thickness of from about 1 µm to about 40 µm, or more specifically in the range of from about 1.5 µm to about 20 µm, respectively.

The swelling of the coating can be controlled using one or more methods, such as by increasing the relative amount of fluorine atoms to the total amount of polymeric material in the coating composition, and/or by increasing the relative amount of reacted photogroups to the total amount of polymeric material in the coating composition.

In some cases, the coating can be described by its capacity to absorb a certain amount of water when hydrated. Such analysis can be carried out by immersing the coated article in water, or a desired buffered solution for a period of time that allows it to become fully hydrated. After the coating is fully hydrated it is removed from the liquid and the amount of water absorbed per amount of coating material, or per an area of the coating is determined.

A fluoropolymer coating provides the surface of the article with lubricity. As used herein, the term "lubricity" refers to a characterization of the frictional force associated with a coating. A coating with improved lubricity has a lower frictional force. Also, in many aspects, the coating has improved durability. As used herein, the term "durability" refers to the wear resistance of a polymer coating, or the ability of a coating to adhere to a device surface when subjected to forces typically encountered during use (for example, normal force, shear force, and the like). A more durable coating is less easily removed from a substrate by abrasion. Durability of a coating can be assessed by subjecting the device to conditions that simulate use conditions. Increased durability can be seen when the coated device is subject to mechanical or physical challenge, such as manipulation of the coated device by bending, twisting, or turning, and/or when the device is in contact with a portion of the body or a portion of another medical article.

In some aspects, the formed coatings can have a lubricity of about 10 g or less. In some aspects the lubricity can be in the range of from about 5 g to about 10 g.

The fluoropolymer-coated catheter can be subjected to one or more various analytical procedures to assess the lubricity and durability of the coating. For example, the fluoropolymer-coated substrates can be evaluated for lubricity/durability by friction measurements using a Vertical Pinch Method, as described in U.S. Pat. No. 7,348,055 (Chappa, et al.) with the following modifications. Coated substrates samples can be inserted into the end of a rod holder, placed between the two jaws of a pinch tester, and immersed in a cylinder of water or saline. The jaws of the pinch tester can be closed with the sample pulled in a vertical direction and opened when the coated sample is returned to the original position. A 500 g force can be applied as the coated substrates are pulled up through the pinched jaws. The pull force exerted on the substrate can then be measured (grams). Pull force (g) is equal to the coefficient of friction (COF) multiplied by pinch force (g).

After the fluoropolymer-containing coating has been formed on the surface of a device (such as a catheter, for example) the coated device can optionally be sterilized prior to use. While any type of sterilization procedure can be employed, one exemplary sterilization procedure involves treatment with ethylene oxide.

Sterilization with ethylene oxide offers the advantage of avoiding the higher temperatures or the moisture associated with steam sterilization. Another advantage of ethylene oxide is that its residues volatilize relatively quickly from the article sterilized. Since ethylene oxide is a highly flammable material it is generally used in a mixture with a flame retardant. Commonly used flame retardant compounds include chlorofluorocarbons (CFCs) such as dichlorodifluoro-methane (also known as CFC 12), and carbon dioxide. Other components that can be present in mixture with ethylene oxide include inert nitrogen gas, which may be used to increase the pressure in the sterilization chamber.

An exemplary ethylene oxide sterilization is carried out as follows. The coated device is place in a commercially available sterilization chamber. The chamber is then heated to a temperature within the range of from about 54° C. (130° F.) to about 60° C. (140° F.). A partial vacuum is created in the chamber with the addition of water vapor to provide a relative humidity in the range of from about 30 to about 80 percent. The sterilant mixture is then converted to a vapor and introduced into the sterilization chamber at a pressure in the range of from about 362.0 millimeter of mercury (0° C.; 7 psi) to about 1706.6 millimeter of mercury (0° C.; 33 psi). The sterilization time can vary and is dependent upon a number of factors including temperature, pressure, humidity level, the specific sterilant mixture employed, and the coated device. Following exposure the ethylene oxide is evacuated from the chamber, for example, by flushing with air, nitrogen, steam or carbon dioxide.

The fluoropolymer-coated catheter can be used for cardiac catheterization. Cardiac catheterization includes procedures such as coronary angiography, as well as left ventrical angiography. Once the catheter is in place, it can be used to perform a number of procedures including angioplasty, angiography, and balloon septostomy.

The fluoropolymer-coated catheter can be used in various analytic procedures, such as measuring blood pressure within the heart, blood oxygenation, and the contractile patterns and strength of cardiac muscle. The fluoropolymer-coated catheter can also be used in procedures to inject dye into the coronary arteries, such as coronary angiography or coronary arteriography. In this process, a catheter having the fluoropolymer coating is inserted using a guidewire and advanced towards the heart to a position above the aortic valve. The guidewire is then removed. The catheter is then engaged with the origin of the coronary artery (either left main stem or right coronary artery) and x-ray opaque iodine-based contrast is injected to make the coronary vessels show up on the x-ray fluoroscopy image.

The fluoropolymer-coated catheter can also be used in balloon-based procedures such as coronary angioplasty (e.g., percutaneous coronary intervention [PCI]).

As another example, the fluoropolymer-containing coatings of the invention can be formed on the surface of an endoscopic sheath. Endoscopic sheaths can be used in various medical procedures, including those involving the urogenital tract, the gastrointestinal tract, and the vasculature. For example an endoscope can be delivered through an endoscopic sheath. Fluoropolymer coatings on the internal and external walls of the endoscopic sheath can facilitate movement of the sheath in the body and the device within the sheath.

Fluoropolymer-containing coatings of the invention can be used in other methods to reduce the friction forces encountered during movement of an insertable or implantable medical device in the body.

EXAMPLE 1

Synthesis of PVP(93.4%)-co-Trifluoroethyl methacrylate(5%)-co-APMA(1%)-co-BBA-APMA(0.6%)

Into a 100 mL vessel, N-vinylpyrrolidinone (5.0 g, 44.99 mmol) was added and dissolved into deionized water (25 mL). Trifluoroethyl methacrylate (337 µL, 2.37 mmol) and aminopropyl methacrylamide hydrochloride (APMA) (8.4 mg, 47.2 µmol) were also dissolved into the reaction mixture which was stirred magnetically at room temperature. 4-Benzoyl-N-(3-methacrylamidopropyl)benzamide (BBA-APMA) (98.8 mg, 0.283 mmol) was dissolved in ethanol (10 mL). When all reagents were solubilized, the solution was degassed under Nitrogen gas for 5 minutes. At this time, 2,2'-Azobis(2-methylpropionitrile) (AIBN) (14 mg, 85.3 µmol) was weighed and added to the solution. The vessel was heated at 55° C. for 48 hours. The solution was then dialyzed in SpectraPor7 MWCO 3500 dialysis tubing to remove the solvent and unreacted monomer. The solution after two days of dialysis was slightly cloudy and colorless. The product was lyophilized to dryness to obtain a white fluffy powder.

EXAMPLE 2

Synthesis of PVP(93.4%)-co-Pentafluoropropyl methacrylate(5%)-co-APMA(1%)-co-BBA-APMA (0.6%)

Into a 100 mL vessel, N-vinylpyrrolidinone (5.0 g, 44.99 mmol) was added and dissolved into deionized water (25 mL). Pentafluoropropyl methacrylate (404 µL, 2.37 mmol) and aminopropyl methacrylamide hydrochloride (APMA) (84.0 mg, 47.2 µmol) were also dissolved into the reaction mixture which was stirred magnetically at room temperature. 4-Benzoyl-N-(3-methacrylamidopropyl)benzamide (BBA-APMA) (98.8 mg, 0.283 mmol) was dissolved in ethanol (10 mL). When all reagents were solubilized, the solution was degassed under Nitrogen gas for 5 minutes. At this time, 2,2'-Azobis(2-methylpropionitrile) (AIBN) (14 mg, 85.3 µmol) was weighed and added to the solution. The vessel was heated at 55° C. for 48 hours. The solution was then dialyzed in SpectraPor7 MWCO 3500 dialysis tubing to remove the solvent and unreacted monomer. The solution after two days of dialysis was slightly cloudy and colorless. The product was lyophilized to dryness to obtain a white fluffy powder.

EXAMPLE 3

Synthesis of PVP(93.4%)-co-Heptafluorobutyl methacrylate(5%)-co-APMA(1%)-co-BBA-APMA(0.6%)

Into a 100 mL vessel, N-vinylpyrrolidinone (5.0 g, 44.99 mmol) was added and dissolved into deionized water (25 mL). Heptafluorobutyl methacrylate (472 µL, 2.37 mmol) and aminopropyl methacrylamide hydrochloride (APMA) (8.4 mg, 47.2 µmol) were also dissolved into the reaction mixture which was stirred magnetically at room temperature. 4-Benzoyl-N-(3-methacrylamidopropyl)benzamide (BBA-APMA) (98.8 mg, 0.283 mmol) was dissolved in ethanol (10 mL). When all reagents were solubilized, the solution was degassed under Nitrogen gas for 5 minutes. At this time, 2,2'-Azobis(2-methylpropionitrile) (AIBN) (14 mg, 85.3 µmol) was weighed and added to the solution. The vessel was heated at 55° C. for 48 hours. The solution was then dialyzed in SpectraPor7 MWCO 3500 dialysis tubing to remove the solvent and unreacted monomer. The solution after two days of dialysis was a white milky solution. The product was lyophilized to dryness to obtain a white fluffy powder.

EXAMPLE 4

Synthesis of PVP(93.4%)-co-Octafluoropentyl methacrylate(5%)-co-APMA(1%)-co-BBA-APMA(0.6%)

Into a 100 mL vessel, N-vinylpyrrolidinone (5.0 g, 44.99 mmol) was added and dissolved into deionized water (25 mL). Octafluoropentyl methacrylate (496 µL, 2.37 mmol) and aminopropyl methacrylamide hydrochloride (APMA) (8.4 mg, 47.2 µmol) were also dissolved into the reaction mixture which was stirred magnetically at room temperature. 4-Benzoyl-N-(3-methacrylamidopropyl)benzamide (BBA-APMA) (98.8 mg, 0.283 mmol) was dissolved in ethanol (10 mL). When all reagents were solubilized, the solution was degassed under Nitrogen gas for 5 minutes. At this time, 2,2'-Azobis(2-methylpropionitrile) (AIBN) (14 mg, 85.3 µmol) was weighed and added to the solution. The vessel was heated at 55° C. for 48 hours. The solution was then dialyzed in SpectraPor7 MWCO 3500 dialysis tubing to remove the solvent and unreacted monomer. The solution after two days of dialysis was slightly cloudy and colorless. The product was lyophilized to dryness to obtain a white fluffy powder.

EXAMPLE 5

Synthesis of PVP(81%)-co-Octafluoropentyl methacrylate(15%)-co-APMA(2%)-co-BBA-APMA(2%)

Into a 100 mL vessel, N-vinylpyrrolidinone (5.0 g, 44.99 mmol) was added and dissolved into deionized water (25 mL). Octafluoropentyl methacrylate (1.75 mL, 8.33 mmol) and aminopropyl methacrylamide hydrochloride (APMA) (198 mg, 1.11 mmol) were also dissolved into the reaction mixture which was stirred magnetically at room temperature. 4-Benzoyl-N-(3-methacrylamidopropyl)benzamide (BBA-APMA) (387 mg, 1.11 mmol) was dissolved in ethanol (15 mL). When all reagents were solubilized, the solution was degassed under Nitrogen gas for 5 minutes. At this time, 2,2'-Azobis(2-methylpropionitrile) (AIBN) (9.6 mg, 58.4 µmol) was weighed and added to the solution. The vessel was heated at 55° C. for 48 hours. The solution was then dialyzed in SpectraPor7 MWCO 3500 dialysis tubing to remove the solvent and unreacted monomer. The solution after two days of dialysis was slightly cloudy and colorless. The product was lyophilized to dryness to obtain a white fluffy powder.

EXAMPLE 6

Synthesis of PVP(81%)-co-Trifluoroethyl methacrylate(15%)-co-APMA(2%)-co-BBA-APMA(2%)

Into a 100 mL vessel, N-vinylpyrrolidinone (5.0 g, 44.99 mmol) was added and dissolved into deionized water (25 mL). Trifluoroethyl methacrylate (1.18 mL, 8.33 mmol) and aminopropyl methacrylamide hydrochloride (APMA) (198 mg, 1.11 mmol) were also dissolved into the reaction mixture which was stirred magnetically at room temperature. 4-Benzoyl-N-(3-methacrylamidopropyl)benzamide (BBA-APMA) (387 mg, 1.11 mmol) was dissolved in ethanol (5 mL) and tetrahydrofuran (15 mL). When all reagents were solubilized, the solution was degassed under vacuum for 45 minutes. At this time, 2,2'-Azobis(2-methylpropionitrile) (AIBN) (9.6 mg, 58.4 µmol) was weighed and added to the solution. The vessel was heated at 51° C. for 18 hours. The solution was then dialyzed in SpectraPor7 MWCO 3500 dialysis tubing to remove the solvent and unreacted monomer. The solution after two days of dialysis was slightly cloudy and colorless. The product was lyophilized to dryness to obtain a white fluffy powder.

EXAMPLE 7

Synthesis of PVP(81%)-co-Pentafluoropropyl methacrylate(15%)-co-APMA(2%)-co-BBA-APMA(2%)

Into a 100 mL vessel, N-vinylpyrrolidinone (5.0 g, 44.99 mmol) was added and dissolved into deionized water (25 mL). Pentafluoropropyl methacrylate (1.42 mL, 8.33 mmol) and aminopropyl methacrylamide hydrochloride (APMA) (198 mg, 1.11 mmol) were also dissolved into the reaction mixture which was stirred magnetically at room temperature. 4-Benzoyl-N-(3-methacrylamidopropyl)benzamide (BBA-APMA) (387 mg, 1.11 mmol) was dissolved in ethanol (5 mL) and tetrahydrofuran (15 mL). When all reagents were solubilized, the solution was degassed under vacuum for 45 minutes. At this time, 2,2'-Azobis(2-methylpropionitrile) (AIBN) (9.6 mg, 58.4 µmol) was weighed and added to the solution. The vessel was heated at 51° C. for 18 hours. The solution was then dialyzed in SpectraPor7 MWCO 3500 dialysis tubing to remove the solvent and unreacted monomer. The solution after two days of dialysis was slightly cloudy and colorless. The product was lyophilized to dryness to obtain a white fluffy powder.

EXAMPLE 8

Synthesis of PVP(81%)-co-Heptafluorobutyl methacrylate(15%)-co-APMA(2%)-co-BBA-APMA(2%)

Into a 100 mL vessel, N-vinylpyrrolidinone (5.0 g, 44.99 mmol) was added and dissolved into deionized water (25 mL). Heptafluorobutyl methacrylate (1.66 mL, 8.33 mmol) and aminopropyl methacrylamide hydrochloride (APMA) (198 mg, 1.11 mmol) were also dissolved into the reaction mixture which was stirred magnetically at room temperature. 4-Benzoyl-N-(3-methacrylamidopropyl)benzamide (BBA-APMA) (387 mg, 1.11 mmol) was dissolved in ethanol (5 mL) and tetrahydrofuran (15 mL). When all reagents were solubilized, the solution was degassed under vacuum for 45 minutes. At this time, 2,2'-Azobis(2-methylpropionitrile) (AIBN) (9.6 mg, 58.4 µmol) was weighed and added to the solution. The vessel was heated at 51° C. for 18 hours. The solution was then dialyzed in SpectraPor7 MWCO 3500 dialysis tubing to remove the solvent and unreacted monomer. The solution after two days of dialysis was slightly cloudy and colorless. The product was lyophilized to dryness to obtain a white fluffy powder.

EXAMPLE 9

Synthesis of PVP(81%)-co-Octafluoropentyl methacrylate(15%)-co-APMA(2%)-co-BBA-APMA(2%)

Into a 100 mL vessel, N-vinylpyrrolidinone (5.0 g, 44.99 mmol) was added and dissolved into deionized water (25 mL). Octafluoropentyl methacrylate (1.75 mL, 8.33 mmol) and aminopropyl methacrylamide hydrochloride (APMA) (198 mg, 1.11 mmol) were also dissolved into the reaction mixture which was stirred magnetically at room temperature. 4-Benzoyl-N-(3-methacrylamidopropyl)benzamide (BBA-APMA) (387 mg, 1.11 mmol) was dissolved in ethanol (5 mL) and tetrahydrofuran (15 mL). When all reagents were solubilized, the solution was degassed under vacuum for 45 minutes. At this time, 2,2'-Azobis(2-methylpropionitrile) (AIBN) (9.6 mg, 58.4 µmol) was weighed and added to the solution. The vessel was heated at 51° C. for 18 hours. The solution was then dialyzed in SpectraPor7 MWCO 3500 dialysis tubing to remove the solvent and unreacted monomer. The solution after two days of dialysis was slightly cloudy and colorless. The product was lyophilized to dryness to obtain a white fluffy powder.

EXAMPLE 10

Synthesis of PVP(85%)-co-Octafluoropentyl methacrylate(8%)-co-AMPS(5%)-co-BBA-APMA(2%)

Into a 100 mL vessel, N-vinylpyrrolidinone (10.0 g, 89.98 mmol) was added and dissolved into dimethylsulfoxide (DMSO) (150 mL). Octafluoropentyl methacrylate (1.78 mL, 8.47 mmol) and 2-acrylamido-2-methylpropanesulfonic acid (AMPS) (2.42 g, 5.29 mmol) were also dissolved into the reaction mixture which was stirred magnetically at room temperature. 4-Benzoyl-N-(3-methacrylamidopropyl)benzamide (BBA-APMA) (738 mg, 2.12 mmol) was added lastly. When all reagents were solubilized, the solution was degassed under vacuum for 90 minutes and purged with nitrogen gas for 3 minutes.

At this time, 2,2'-Azobis(2-methylpropionitrile) (AIBN) (20 mg, 122 µmol) was weighed and added to the solution. The vessel was heated at 55° C. for 72 hours. The solution was then dialyzed in SpectraPor7 MWCO 3500 dialysis tubing to remove the DMSO and unreacted monomer. The solution after two days of dialysis was slightly cloudy and colorless. The product was lyophilized to dryness to obtain a white fluffy powder.

EXAMPLE 11

Synthesis of PVP(85%)-co-Trifluoroethyl methacrylate(8%)-co-AMPS(5%)-co-BBA-APMA(2%)

Into a 100 mL vessel, N-vinylpyrrolidinone (5.0 g, 44.99 mmol) was added and dissolved into dimethylsulfoxide (DMSO) (40 mL). Trifluoroethyl methacrylate (603 µL, 4.23 mmol) and 2-acrylamido-2-methylpropanesulfonic acid (AMPS) (1.21 g, 2.65 mmol) were also dissolved into the reaction mixture which was stirred magnetically at room temperature. 4-Benzoyl-N-(3-methacrylamidopropyl)benzamide (BBA-APMA) (370 mg, 1.06 mmol) was added lastly. When all reagents were solubilized, the solution was degassed under vacuum for 90 minutes and purged with nitrogen gas for 3 minutes. At this time, 2,2'-Azobis(2-methylpropionitrile) (AIBN) (20 mg, 122 µmol) was weighed and added to the solution. The vessel was heated at 55° C. for 18 hours. The solution was then dialyzed in SpectraPor7 MWCO 3500 dialysis tubing to remove the DMSO and unreacted monomer. The solution after two days of dialysis was slightly cloudy and colorless. The product was lyophilized to dryness to obtain a white fluffy powder.

EXAMPLE 12

Synthesis of PVP(85%)-co-Pentafluoropropyl methacrylate(8%)-co-AMPS(5%)-co-BBA-APMA(2%)

Into a 100 mL vessel, N-vinylpyrrolidinone (5.0 g, 44.99 mmol) was added and dissolved into dimethylsulfoxide (DMSO) (40 mL). Pentafluoropropyl methacrylate (722 µL, 4.23 mmol) and 2-acrylamido-2-methylpropanesulfonic acid (AMPS) (1.21 g, 2.65 mmol) were also dissolved into the reaction mixture which was stirred magnetically at room temperature. 4-Benzoyl-N-(3-methacrylamidopropyl)benzamide (BBA-APMA) (370 mg, 1.06 mmol) was added lastly. When all reagents were solubilized, the solution was degassed under vacuum for 90 minutes and purged with nitrogen gas for 3 minutes. At this time, 2,2'-Azobis(2-methylpropionitrile) (AIBN) (20 mg, 122 µmol) was weighed and added to the solution. The vessel was heated at 55° C. for 18 hours. The solution was then dialyzed in SpectraPor7 MWCO 3500 dialysis tubing to remove the DMSO and unreacted monomer. The solution after two days of dialysis was slightly cloudy and colorless. The product was lyophilized to dryness to obtain a white fluffy powder.

EXAMPLE 13

Synthesis of PVP(85%)-co-Heptafluorobutyl methacrylate(8%)-co-AMPS(5%)-co-BBA-APMA(2%)

Into a 100 mL vessel, N-vinylpyrrolidinone (5.0 g, 44.99 mmol) was added and dissolved into dimethylsulfoxide (DMSO) (40 mL). Heptafluorobutyl methacrylate (844 pt, 4.23 mmol) and 2-acrylamido-2-methylpropanesulfonic acid (AMPS) (1.21 g, 2.65 mmol) were also dissolved into the reaction mixture which was stirred magnetically at room temperature. 4-Benzoyl-N-(3-methacrylamidopropyl)benzamide (BBA-APMA) (370 mg, 1.06 mmol) was added lastly. When all reagents were solubilized, the solution was degassed under vacuum for 90 minutes and purged with nitrogen gas for 3 minutes. At this time, 2,2'-Azobis(2-methylpropionitrile) (AIBN) (20 mg, 122 µmol) was weighed and added to the solution. The vessel was heated at 55° C. for 18 hours. The solution was then dialyzed in SpectraPor7 MWCO 3500 dialysis tubing to remove the DMSO and unreacted monomer. The solution after two days of dialysis was slightly cloudy and colorless. The product was lyophilized to dryness to obtain a white fluffy powder.

EXAMPLE 14

Synthesis of Polyacrylamide(85%)-co-Trifluoroethyl methacrylate(8%)-co-AMPS(5%)-co-BBA-APMA (2%)

Into a 100 mL vessel, acrylamide (5.0 g, 44.99 mmol) was added and dissolved into dimethylsulfoxide (DMSO) (40 mL). Heptafluorobutyl methacrylate (844 µL, 4.23 mmol) and 2-acrylamido-2-methylpropanesulfonic acid (AMPS) (1.21 g, 2.65 mmol) were also dissolved into the reaction mixture which was stirred magnetically at room temperature. 4-Benzoyl-N-(3-methacrylamidopropyl)benzamide (BBA-APMA) (370 mg, 1.06 mmol) was added lastly. When all reagents were solubilized, the solution was degassed under vacuum for 90 minutes and purged with nitrogen gas for 3 minutes. At this time, 2,2'-Azobis(2-methylpropionitrile) (AIBN) (20 mg, 122 µmol) was weighed and added to the solution. The vessel was heated at 55° C. for 18 hours. The solution was then dialyzed in SpectraPor7 MWCO 3500 dialysis tubing to remove the DMSO and unreacted monomer. The solution after two days of dialysis was slightly cloudy and colorless. The product was lyophilized to dryness to obtain a white fluffy powder.

EXAMPLE 15

UV-Crosslinked Fluoropolymer Coatings

Coating solutions comprised a photo-derivatized poly(vinyl pyrrolidone) (PVP) with fluorinated groups (8 fluorine atoms, 8 mol % substitution), PVP K90, PVP K30, and a multifunctional photocrosslinking reagent in a ratio of 10/20/40/1.5 mg/mL in a mixture of water and isopropanol (IPA). Coating solutions were prepared in a water:IPA mixture of 2:3. A control solution was prepared in which the fluorinated PVP was replaced with a photo-derivatized PVP that lacked fluorinated groups.

30-cm Pebax rods were cleaned with isopropanol and dried before coating. Parts were coated by dipping 15 cm of each part into the coating solution, dwelling 3 s, and withdrawing from solution at a rate of 0.5 cm/s. Coatings were dried at ambient conditions and UV cured for 3 min.

The wet-to-dry lubricity of each coating was assessed as follows. The lower 9 cm of each coated Pebax rod was placed in water for 60 seconds, removed from the water and pinched between two silicone pads with a force of 250 g. The measured was the force necessary to pull the part through the pads at a rate of 1.0 cm/s. Data reported was the average of three separate runs. Each sample was tested in the same orientation/position 15 times to assess durability of the coating. The results of durability were as follows: coatings of the control group without any fluoropolymer were the least durable, and coatings formed from fluoropolymer compositions (coated at 20 mg/mL) were more durable than those formed from fluoropolymer compositions (coated at 10 mg/mL).

What is claimed is:

1. An implantable or insertable medical device comprising a lubricious coating comprising one or more polymers comprising at least one water soluble fluoropolymer;
    wherein the fluoropolymer has a polymeric backbone and comprises:
    a fluorinated monomer comprising fluorine atoms, wherein the majority or all of the fluorine atoms in the fluorinated monomer are not directly covalently attached to an atom of the polymer backbone;
    the coating further comprising a non-fluorinated hydrophilic monomer present in the fluoropolymer, in a second polymer, or both in the fluoropolymer and second polymer; and
    an ultraviolet light (UV)-reacted group covalently bonded to a target moiety, the UV-reacted group present in the fluoropolymer, in a second polymer, or in a non-polymeric compound, and wherein the non-fluorinated hydrophilic monomer is present in the coating in an amount by weight greater than the fluorinated monomer.

2. The device of claim 1, wherein the fluoropolymer has no fluorine atoms directly covalently attached to an atom of the polymer backbone.

3. The device of claim 1, wherein the fluorinated monomer is present in the fluoropolymer in an amount in the range of from about 1% wt to about 40% wt.

4. The device of claim 3, wherein the fluorinated monomer is present in the fluoropolymer in an amount in the range of from about 5% wt to about 30% wt.

5. The device of claim 1, wherein the fluorine atoms that are not directly covalently attached to an atom of the polymer backbone are present in the fluoropolymer in an amount in the range of from about 0.2 mmol/gram to about 11 mmol/gram.

6. The device of claim 5, wherein the fluorine atoms that are not directly covalently attached to an atom of the polymer backbone are present in the fluoropolymer in an amount in the range of from about 1 mmol/gram to about 6.5 mmol/gram.

7. The device of claim 1, wherein the fluorinated monomer is of formula I:

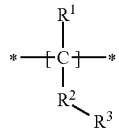

wherein $R^1$ is —H, —F, —CH$_3$, or —CH$_2$CH$_3$,
$R^2$ is (a covalent bond), or a non-fluorinated linking group comprising one or more of C, O, N, S, or mixtures thereof and
$R^3$ is a fluorocarbon group.

8. The device of claim 7, wherein the fluorinated monomer comprises at least 2 fluorine atoms that are not directly covalently attached to an atom of a polymer backbone.

9. The device of claim 8, wherein the fluorinated monomer comprises from 2-10 fluorine atoms that are not directly covalently attached to an atom of a polymer backbone.

10. The device of claim 7 where, in formula I, $R^2$ is selected from the group consisting of —C(O)O—, —C(O)N—, —CH$_2$O—, —O—, and —(CH$_2$)$_z$—, wherein z in an integer in the range of 1 to 4.

11. The device of claim 10 where, in formula I, $R^2$ is —C(O)O—.

12. The device of claim 7 where, in formula I, $R^3$ is a linear, branched, or cyclic fluorocarbon group having 1-24 carbon atoms, 2-48 fluorine atoms, and 0-48 hydrogen atoms.

13. The device of claim 7 where, in formula I, $R^3$ is —(CR$^4$R$^5$)$_q$CR$^6$R$^7$R$^8$, where $R^4$, $R^5$, $R^6$, $R^7$, and $R^8$, are independently selected from H and F, provided that at least two of $R^4$, $R^5$, $R^6$, $R^7$, and $R^8$, are F, and wherein q is in the range of 0 to 20.

14. The device of claim 7 wherein the fluorinated monomer is selected from the group consisting of 2,2,2-trifluoroethyl(meth)acrylate, 2,2,3,3,3-pentafluoropropyl(meth)acrylate, 1,1,1,3,3,3-hexafluoroisopropyl(meth)acrylate, and 2,2,3,3,4,4,5,5-octafluoropentyl(meth)acrylate.

15. The device of claim 1, wherein the non-fluorinated hydrophilic monomer is present in the polymeric backbone of the fluoropolymer.

16. The device of claim 15, wherein the non-fluorinated hydrophilic monomer is present in the fluoropolymer in an amount in the range of 60% wt to 99% wt of the fluoropolymer.

17. The device of claim 16, wherein the non-fluorinated hydrophilic monomer is present in the fluoropolymer in an amount in the range of from about 70% wt to about 95% wt of the fluoropolymer.

18. The device of claim 1, wherein the non-fluorinated hydrophilic monomer comprises vinyl pyrrolidone.

19. The device of claim 1, wherein the UV-reacted group is present as a pendent group on the polymeric backbone of the fluoropolymer.

20. The device of claim 1, wherein the coating has a thickness in the range of from about 0.5 μm to about 10 μm in a dried state, and in the range of from about 1 μm to about 40 μm in a fully hydrated state.

21. The device of claim 1 comprising a catheter, wherein the coating is present on at least a portion the catheter surface.

22. The device of claim 1, wherein the fluoropolymer has as solubility in water of 1 mg/mL or greater.

\* \* \* \* \*